United States Patent [19]

Hajime

[11] 4,435,641

[45] Mar. 6, 1984

[54] INSPECTION APPARATUS FOR INSPECTING AN OBJECT TO DETERMINE WHETHER OR NOT IT CONTAINS AN ABNORMALITY, DEFECT OR THE LIKE

[75] Inventor: Yoshida Hajime, Tokyo, Japan

[73] Assignee: Hajime Industries Ltd., Japan

[21] Appl. No.: 265,652

[22] Filed: May 20, 1981

[30] Foreign Application Priority Data

Oct. 15, 1980 [JP] Japan .................................. 55-144046

[51] Int. Cl.³ ............................................. H01J 40/14
[52] U.S. Cl. ................................... 250/223 B; 356/240
[58] Field of Search .................... 250/223 B, 572, 216; 350/437, 440, 558, 31, 482; 356/240, 239

[56] References Cited

U.S. PATENT DOCUMENTS 3,004,420 10/1961 Ruhle .................................. 350/437
3,778,617 12/1973 Calhoun ........................ 250/223 B Primary Examiner—David C. Nelms
Assistant Examiner—J. Jon Brophy

[57] ABSTRACT

An apparatus is disclosed which inspects whether or not an object to be inspected contains an abnormality, defect or the like by using a single photo-sensor such as a video camera provided with a photo-electric conversion screen such as a target screen therein. An inspection section or processor such as an computer is provided to receive the output from the video camera and process the same to determine whether the object contains the abnormality, defect etc. or not. The video camera includes an optical lens arrangement which can simultaneously focus images of at least two different portions of the object on the target screen of the video camera.

8 Claims, 4 Drawing Figures

INSPECTION APPARATUS FOR INSPECTING AN OBJECT TO DETERMINE WHETHER OR NOT IT CONTAINS AN ABNORMALITY, DEFECT OR THE LIKE

BACKGROUND OF THE INVENTION

1. Field of the Invention

The present invention relates generally to an inspection apparatus and, more particularly to an inspection apparatus that makes it possible to simultaneously inspect a plurality of locations, for example, a bottle mouth as well as the bottle bottom.

2. Description of the Prior Art

On production lines of bottle utilization such as in the beverage or pharmaceutical industries and the like, there are the bottle washing process and bottle inspection process as an absolute necessity. Regardless to whether the bottles are new or recycled, after bottle washing, it is necessary prior to using bottles, to detect residual foreign particles or damage at the bottle mouth and bottom. Such inspections are mostly conducted visually. In addition to the inspection of the bottle mouth and bottom, it is further necessary occasionally to also inspect the bottle body.

As a recent trend, instead of the above mentioned visual inspection, mechanical inspection has become adapted as a step to promote inspection automation. Many systems have already been proposed as equipment for such automatic bottle inspection whereas photo-electric conversion sensors such as photodiodes or television cameras or the like are used to detect abnormalities by photo-electric conversion of the optical brightness differences at the inspected zones of the bottle due to damage or abnormal conditions.

However, by such conventinal systems, it was impossible to simultaneously inspect a plurality of sections, such as the bottle mouth, bottle bottom or bottle body, etc. by one photo-electric conversion sensor. In other words, for instance, three separate photo-electric conversion sensors are used in order to inspect the three points of bottle mouth, bottom and body, by which three separate photo-electric conversions for respective inspected places will have to be conducted, which outputs were fed into three separate inspection units in order to conduct the inspection. Therefore, conventional systems contain the deflect that they tend to be complicated and high cast.

OBJECTS AND SUMMARY OF THE INVENTION

Accordingly, it is a main purpose of the present invention to provide an inspection apparatus that can simultaneously inspect a plurality of different places, such as the bottle mouth and the bottle bottom by a single photo-electric conversion sensor.

According to an aspect of the present invention, an inspection apparatus for inspecting whether or not an object contains an abnormality, defect or the like is provided which comprises:

(a) a photo-sensor having a photo-electric screen, picking up a portion of the object to be inspected and producing a corresponding electrical signal; and (b) a detector section receiving the electrical signal from said photo-sensor to determine whether or not said object contains abnormalities defects or the like, said photo-sensor having an optical lens arrangement which can simultaneously focus images of at least two different portions of said object on said photo-electric conversion screen of said photo-sensor.

The other objects, features and advantages of the present invention will become apparent from the following description taken in conjunction with the accompanying drawings through which the like references designate the same elements and parts.

DESCRIPTION OF THE PREFERRED EMBODIMENTS

The present invention will be hereinafter described with reference to the attached drawings.

Figure 1:
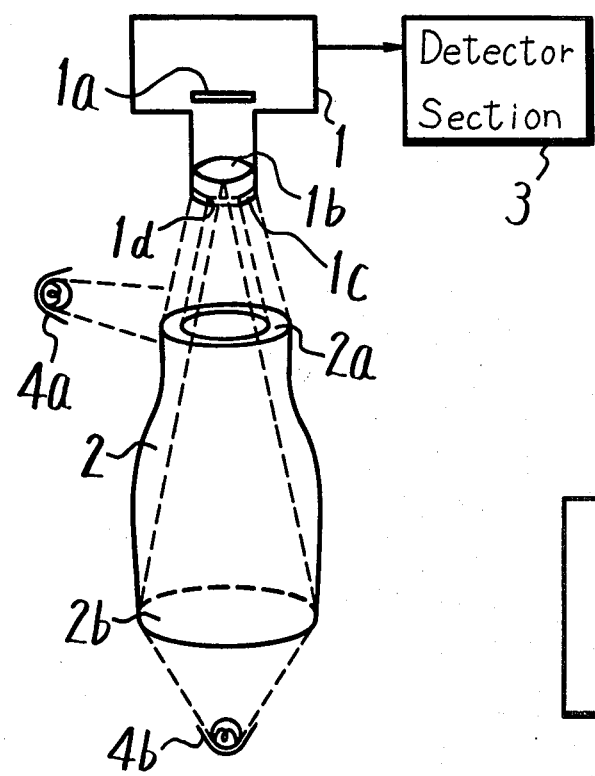
FIG. 1 is a schematic diagram illustrating an example of the inspection apparatus according to the present invention.

FIG. 1 illustrates a schematic diagram of one example of the present invention in which reference numeral 1 designates an optical or photo-electric conversion sensor such as a video camera or the like. In the video camera 1, a photo-electric conversion or target screen 1a serving as the photo-electric conversion element and two optical lens arrangements 1b and 1c which are located on the same optical axis at a predetermined distance are provided.

The electric signal from the photosensor 1, which corresponds to the optical images as focussed on photo-electric conversion screen 1a from an object 2 to be inspected through lens arrangements 1b and 1c, is fed to a detector section 3 such as a computer which contains an amplifier and detection circuitry and so on. Such detector section 3 may utilize such conventionally known means and detail description thereof will be omitted in order to simplify matters.

A bottle is illustrated as the object 2 to be inspected in the examle of the present invention, as shown on FIG. 1. In this example, a bottle mouth 2a and a bottle bottom 2b of the bottle 2 are inspected at the same time. For such purpose, light source 4a that irradiates upon the bottle mouth 2a, as well as light source 4b which irradiates through the bottle bottom 2b are respectively arranged. Such light sources may be limited to one only or none as desired.

Now, in the case of the example of the present invention as shown on FIG. 1, one optical lens arrangement 1b is a disc type convex lens as an example which has such a focal length so that the image of bottle bottom 2b of bottle 2, which is placed at a predetermined distance to photosensor 1, is formed on the screen 1a of the photosensor 1, while the other optical lens arrangement 1c is a ring shaped convex lens that has a focal distance to form the image of the bottle mouth 2a of the same bottle 2 on the screen 1a in combination with convex lens 1b and has a center opening 1d of a dimension that does not disturb the image of the bottle bottom 2b focused by lens 1b. This lens arrangement 1c is located, for example, at the front side of lens 1b, in other words, at the side of the bottle 2, with both optical axes of the lens arrangements 1b and 1c being coincident to each other. Accordingly, by lens 1b and 1c, the images of two different places, which are the bottle bottom 2b and the bottle mouth 2a, simultaneously are focussed on the screen 1a of the photosensor 1 as shown on FIG. 2.

Figure 2:
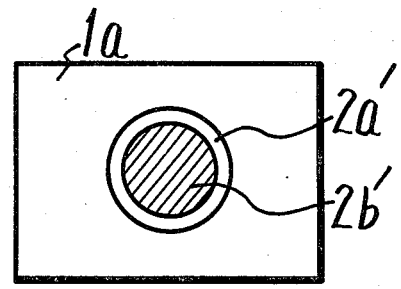
FIG. 2 is a plan view which is used to explain the operation of the invention shown in FIG. 1.

In other words, FIG. 2 is an enlarged plane view of the photo-electric conversion screen 1a of the photosensor 1 on which 2b is the formed image of bottle bottom 2b by lens 1b, and 2a' is the formed image of bottle mouth 2a by the combination of the lens 1c and 1b. As apparent from the drawing, the arrangement for placement of lens 1b and 1c is so selected that there is hardly any duplication of the images 2b' and 2a' on the screen 1a from the bottle bottom 2b and bottle mouth 2a and that image 2a' is formed on the outside and closely neighbouring to image 2b'.

As such, by scanning screen 1a with an electronic beam as commonly known, electric signals that correspond to the optical images on screen 1a are obtained. The electric signals are then fed to the detector section 3 from the photosensor 1 such as video cameras, where detection of such above mentioned abnormalities or defects of the bottle mouth 2a as well as bottle 2b is performed based on such electric signals from the video camera 1. In other words, the inspection of two different places, which are the bottle mouth 2a and the bottle bottom 2b, can be simultaneously conducted by using one video camera 1.

Further, since the detector section 3 by which the inspection is done, will depend upon conventionally known equipment such as a computer etc., description of such will be omitted herein.

Figure 3:
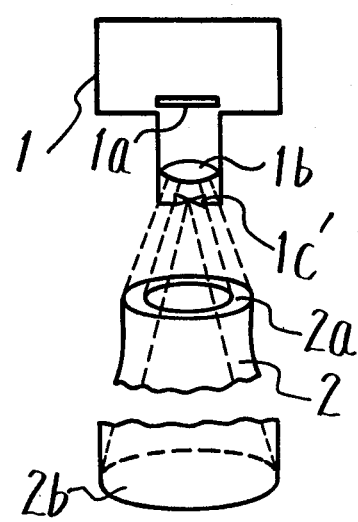
FIG. 3 and FIG. 4 are schematic diagrams respectively that illustrate the main parts of further examples of the present invention.

FIG. 3 is a schematic diagram showing the essence of another example of the present invention. In this example, convex lens 1b forms image 2a' of the bottle mouth 2a on the screen 1a, while a concave lens 1c' is used in lieu of the convex lens 1c in the example of FIG. 1, which forms image 2b' of the bottle bottom 2b on the screen 1a simultaneous to image 2a' in combination with lens 1b according to the relation as shown on FIG. 2. That is, the lens 1b and 1c' are formed and arranged to provide the images 2a' and 2b' as above.

Figure 4:
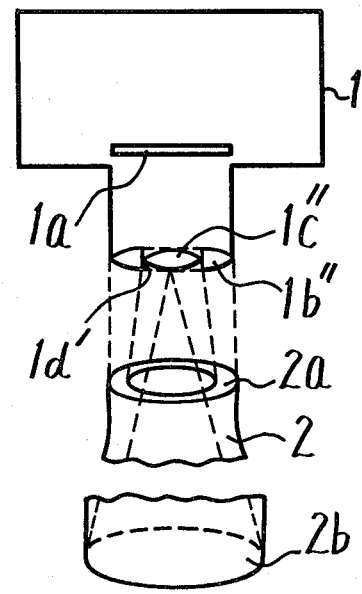

FIG. 4 illustrates a schematic diagram of the essence of a further example of the present invention. In this example, a lens arrangement is used with a normal disc type convex lens 1c" fitted into a center opening 1d' of a ring shaped concave lens 1b" as an example. In this case, the focal lengths and so on of lens 1b" and 1a" are selected so that lens 1b" forms image 2a' of bottle mouth 2a while lens 1c" forms image 2b' of the bottle bottom 2b simultaneously on screen 1a.

Further, while the above mentioned examples cite cases wherein both of the two lens are single lens, it is needless to say that each lens may be formed of a plural number of elements of a collective lens so as to prevent colour aberration etc.

The above references were examples for simultaneous inspection of portions in two different places, but it is also obvious that three or more places may be simultaneously inspected by arrangement of three or more lens with different focal distances so that the images of three or more different places can be simultaneously formed on a single screen and for inspection by a single video camera.

Further, although not illustrated on the drawings, it is needless to say that optical filters or unnecessary light shielding means may be used in order to acquire sharp images from each lens.

As above stated, by the present invention, the inspection of a plurality of different places at different distances can be conducted by one photosensor simultaneously, in which case the photosensor have be the same structure as conventionally used, and by merely changing the optical lens arrangement and with only one inspection section, the advantages and merits of the invention are unusually great.

It will be apparent that many modifications and variations could be effected by one skilled in the art without departing from the scope or spirit of the novel concepts of the present invention, so that the spirit or scope of the invention should be determined by the appended claims only.

I claim as my invention:

1. An inspection apparatus for inspecting an object to determine whether or not it contains an abnormality, defect or the like, comprising:
   (a) a photo-sensor having a target screen, receiving an image of a portion of the object to be inspected and producing a corresponding electrical signal; and
   (b) a detector section receiving the electrical signal from said photo-sensor to determine whether or not said object contains abnormalities defects or the like, said photo-sensor having an optical lens arrangement which can simultaneously focus images of at least two different portions of said object disposed at different distances from said optical lens arrangement on first and second separate portions of said target screen of said photo-sensor.

2. An inspection apparatus as claimed in claim 1, in which said optical lens arrangement consists of a disc type convex lens and a ring type convex lens concentric with said disc type convex lens.

3. An inspection apparatus as claimed in claim 1, in which said optical lens arrangement consists of a disc type convex lens and a disc type concave lens concentric with said convex lens.

4. An inspection apparatus as claimed in claim 1, in which said optical lens arrangement consists of a disc type lens and a ring type convex lens that is placed around and in contact with the disc type lens.

5. An inspection apparatus for inspecting an object, comprising:
   (a) a photo-sensor having a target screen effective for producing an electrical signal in response to an image thereon;
   (b) a detector section receiving said electrical signal from said photo-sensor;
   (c) an optical lens arrangement having first and second concentric lenses having first and second different focal lengths;
   (d) said first focal length being effective to focus a first image of a first part of said object at a first distance on a first portion of said screen; and
   (e) said second focal length being effective to focus a second image of a second part of said object at a second different distance on a second portion of said screen.

6. An inspection apparatus as claimed in claim 5, in which said first lens is a disc type convex lens and said second lens is ring type convex lens concentric with said first lens.

7. An inspection apparatus as claimed in claim 5, in which said first lens in a disc type convex lens and said second lens is disc type concave lens concentric with said first lens.

8. An inspection apparatus as claimed in claim 5, in which said first lens is a disc type lens and said second lens a ring type convex lens that is placed around the first lens.

* * * * *